United States Patent [19]

Dauth et al.

[11] Patent Number: 5,561,231
[45] Date of Patent: Oct. 1, 1996

[54] HOMOGENEOUS HYDROSILYLATION CATALYSTS

[75] Inventors: Jochen Dauth; Bernward Deubzer; Hans Bindl; Udo Peetz, all of Burghausen, Germany

[73] Assignee: Wacker-Chemie GmbH, Munich, Germany

[21] Appl. No.: 276,922

[22] Filed: Jul. 19, 1994

[30] Foreign Application Priority Data

Jul. 22, 1993 [DE] Germany .................. 43 24 685.0
Mar. 31, 1994 [DE] Germany .................. 44 11 444.3

[51] Int. Cl.$^6$ .................. C07F 15/00; C07F 7/02
[52] U.S. Cl. .................. 546/2; 546/4,12,14; 502/158; 502/161; 556/9; 556/12; 556/14; 556/18; 556/21; 556/137; 556/479; 528/15
[58] Field of Search .................. 556/9,12,14,18,21,137, 556/479; 546/2, 4, 12, 14; 528/15; 502/158, 161

[56] References Cited

U.S. PATENT DOCUMENTS

| | | | |
|---|---|---|---|
| 2,476,166 | 7/1949 | Wayo | 260/399 |
| 3,445,420 | 5/1969 | Kookotsedes et al. | 260/37 |
| 3,795,656 | 3/1974 | Martin | 260/46.5 E |
| 4,398,010 | 8/1983 | Adkins | 528/15 |
| 4,424,332 | 1/1984 | Panster et al. | 528/30 |
| 4,504,645 | 3/1985 | Melancon | 528/15 |
| 5,187,134 | 2/1993 | Panster et al. | 502/158 |
| 5,426,200 | 6/1995 | Dauth et al. | 556/9 |

FOREIGN PATENT DOCUMENTS

| | | |
|---|---|---|
| 0061241 | 9/1982 | European Pat. Off. . |
| 0072435 | 2/1983 | European Pat. Off. . |
| 0546716 | 6/1993 | European Pat. Off. . |

OTHER PUBLICATIONS

C. Hu et al., J. Organomet. Chem. 1986, 307(1), 115.
Derwent Abstract AN 84-053240.

*Primary Examiner*—Porfirio Nazario-Gonzales
*Attorney, Agent, or Firm*—Martin Connaughton

[57] ABSTRACT

Transition metal-containing organosiloxanes of at least three organosiloxane units, comprising at least one transition metal complex, chemically bonded via ligands selected from among amino, phosphino or sulfido groups of Pt, Pd, Rh, Ru, Os or Ir, excluding those organosiloxanes which contain exclusively Pt(O) complexes bonded via amino ligands, are used as homogeneous hydrosilylation catalysts.

8 Claims, No Drawings

HOMOGENEOUS HYDROSILYLATION CATALYSTS

FIELD OF INVENTION

The present invention relates to transition metal-containing organosiloxanes, a process for the preparation thereof, a hydrosilylation process in the presence of the transition metal-containing organosiloxanes and compositions which comprise the transition metal-containing organosiloxanes as homogeneous hydrosilylation catalysts.

BACKGROUND OF INVENTION

It is known that the addition of Si-bonded hydrogen to an aliphatic multiple bond, which is described as hydrosilylation, can be promoted by transition metal catalysts, in particular platinum compounds. EP-A-546 716 describes platinum centers bonded to polysiloxane resins via amino groups and use thereof as heterogeneous hydrosilylation catalysts. Heterogeneous catalysts have to be removed from the product after the reaction, since they impair the product's properties such as transparency and mechanical properties.

Polysiloxane-bonded platinum catalysts for hydrosilylation are known from U.S. Pat. No. 3,795,656. According to the process described therein, chloroplatinic acid is reacted with organosilicon compounds having functional amino groups to give organosilicon compounds containing ammonium-platinum(IV) adducts. These organosilicon compounds possess a strongly polar salt-like structure and for lumps or set solid if they are present in pure form. They can therefore be re-dispersed only with great difficulty and can be homogeneously incorporated in silicones as solutions. Furthermore, the preparation of these organosilicon compounds from strongly polar chloroplatinic acid and a weak polar amino-functional organosilicon compound is problematical because of solubility differences. U.S. Pat. No. 4,398,010 describes the reduction of the above organosilicon compound containing ammonium-platinum(IV) adducts, the platinum(IV) centers being reduced to the oxidation stage zero in the presence of bases. The reduction gives solids which can be used as homogeneous hydrosilylation catalysts only as solutions.

C. Hu et al., J. Organomet. Chem. 1986, 307 (1), 115 describe platinum complexes intended for chemotherapy for the treatment of cancer, which complexes have ethylendiamino-functional silanes or disiloxanes and Cl as ligands. The salt-like potassium tetrachloroplatinate is used as starting material in the synthesis and is carried out in water. The process fails when non-polar relatively high-molecular weight aminofunctional siloxanes are used.

SUMMARY OF INVENTION

It is an object of the present invention to provide hydrosilylation catalysts which can be used homogeneously, neither discolor nor make turbid the product of the hydrosilylation reaction, and can be prepared in a simple way.

The present invention provides transition metal-containing organosiloxanes of at least three organosiloxane units, which comprise at least one transition metal complex, chemically bonded via ligands selected from among amino, phosphino or sulfido groups, of Pt, Pd, Rh, Ru, Os or Ir, excluding those organosiloxanes which contain exclusively Pt(O) complexes bonded via amino ligands.

The present invention also provides a hydrosilylation process, which comprises reacting (A) compounds comprising radicals having aliphatic carbon-carbon multiple bonds, with
(B) compounds having Si-bonded hydrogen atoms, selected from among silanes or siloxanes, or, instead of (A) and (B),
(C) compounds having aliphatic carbon-carbon multiple bonds and Si-bonded hydrogen atoms, in the presence of
(D) transition metal-containing organosiloxanes of the invention as hydrosilylation catalyst.

The transition metal-containing organosiloxanes (D) do not isomerize, or isomerize to only a small extent, the compounds (A) comprising radicals having aliphatic carbon-carbon multiple bonds.

The transition metal-containing organosiloxanes (D) are thermally stable and do not discolor any hydrosilylation products by colloidal transition metal formed in the hydrosilylation.

The transition metal-containing organosiloxanes (D) can be used in all processes for reacting compounds comprising Si-bonded hydrogen atoms with organic compounds having aliphatic multiple bonds, wherein use was made of catalysts which promote the molecular addition of Si-bonded hydrogen to an aliphatic multiple bond. For the purpose of the present invention, organic compounds (A) having aliphatic multiple bonds also include organic compounds having cycloaliphatic multiple bonds.

Examples of compounds (A) having aliphatic multiple bonds are compounds having an aliphatic carbon-carbon double bond, such as styrene, allyl glycidyl ether, allyl cyanide, allyl acetate, allylsuccinic anhydride, glycol monoallyl ether, allyl methacrylate, allylamine and cyclohexene, and compounds having an aliphatic carbon-carbon triple bond, such as acetylene and butynol.

(A) compounds, comprising radicals having aliphatic carbon-carbon multiple bonds, are preferably organopolysiloxanes comprising radicals having aliphatic carbon-carbon multiple bonds.

The organopolysiloxanes (A), which comprise radicals having aliphatic carbon-carbon multiple bonds, are preferably linear or branched organopolysiloxanes of units of the formula

where
$R^1$ is a monovalent hydrocarbon radical free of aliphatic carbon-carbon multiple bonds and having from 1 to 18 carbon atoms per radical and
$R^2$ is a monovalent hydrocarbon radical having an aliphatic carbon-carbon multiple bond and having from 2 to 8 carbon atoms per radical
a is 0, 1, 2 or 3,
b is 0, 1 or 2
and the sum a+b is 0, 1, 2 or 3,
with the proviso that on average there are at least 2 radicals $R^2$ present per molecule.

The organopolysiloxanes (A) preferably possess an average viscosity of from 100 to 10,000 mPa.s at 25° C.

Examples of hydrocarbon radicals $R^1$ are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl radicals and methylcyclohexyl radicals; aryl radicals such as the phenyl, naphthyl, anthryl and phenanthryl radical; alkaryl radicals such as o-, m-, p-tolyl radicals, xylyl radicals and ethylphenyl radicals; and aralkyl radicals such as the benzyl radical, the α- and the β-phenylethyl radical.

Examples of radical $R^2$ are alkenyl radicals such as the vinyl, 5-hexenyl, 1-propenyl, allyl, 1-butenyl and 1-pentenyl radical and alkynyl radicals such as the ethynyl, propargyl and 1-propynyl radical.

Examples of silicon compounds (B) having Si-bonded hydrogen atoms are silanes having one Si-bonded hydrogen atom per molecule such as trichlorosilane, dimethylchlorosilane, dimethylethoxysilane, methyldiethoxysilane, methyldichlorosilane and triethoxysilane, and organopolysiloxanes having at least one Si-bonded hydrogen atom per molecule such as α,w-dihydrogen[dimethylpolysiloxane], tetramethyldisiloxane, tetramethylcyclotetrasiloxane, mixed polymers of trimethylsiloxane and methylhydrogensiloxane units, mixed polymers of trimethylsiloxane, dimethylsiloxane and methylhydrogensiloxane units and trimethylsiloxyhydrogensilane.

The organopolysiloxanes (B), which have Si-bonded hydrogen atoms, are preferably linear, cyclic or branched organopolysiloxanes of units of the formula $$R^1_cH_dSiO_{\frac{4-c-d}{2}} , \quad (2)$$

where
$R^1$ is as defined above,
c is 0, 1, 2 or 3,
d is 0, 1 or 2
and the sum of c+d is 0, 1, 2 or 3,
with the proviso that on average at least 2 Si-bonded hydrogen atoms are present per molecule.

The organopolysiloxanes (B) preferably possess an average viscosity of from 10 to 1000 mPa.s at 25° C.

The compounds (C), which have aliphatic carbon-carbon multiple bonds and Si-bonded hydrogen atoms and can be used instead of compounds (A) and (B), are preferably organopolysiloxanes, in particular those of units of the general formulae $$R^1_eSiO_{\frac{4-e}{2}} , \quad (3)$$

$$R^1_fR^2SiO_{\frac{3-f}{2}} \quad (4)$$

and $$R^1_gHSiO_{\frac{3-g}{2}} , \quad (5)$$

where
$R^1$ and $R^2$ are as defined above,
e is 0, 1, 2 or 3,
f is 0, 1 or 2,
g is 0, 1 or 2.
with the proviso that per molecule there are present on average at least 2 radicals $R^1$ and on average at least 2 Si-bonded hydrogen atoms.

Examples of organopolysiloxanes (C) are those of $SiO_{4/2}$, $R^1_3SiO_{1/2}$, $R^1_2R^2SiO_{1/2}$ and $R^1_2HSiO_{1/2}$ units, so-called MQ resins, with these resins also being able to comprise T units ($R^1SiO_{3/2}$) and D units ($R^1_2SiO$).

The organopolysiloxanes (C) preferably possess an average viscosity of from 100 to 100,000 mPa.s at 25° C. or are solids having molecular weights of from 5000 to 50,000 g/mol.

A particularly good solubility in silicone systems is shown by those organosiloxanes (D) which have at least 5, preferably 35, more preferably 100, organosiloxane units per transition metal atom.

Above a molecular mass of 1000 g/mol, the volatility and migration ability of the organosiloxanes (D) used as hydrosilylation catalysts are very small.

The organosiloxanes (D) are preferably used in amounts of from 1 to 1000 ppm by weight (parts by weight per one million parts by weight), preferably from 10 to 100 ppm by weight, calculated as elemental transition metal Pt, Pd, Ru, Rh, Os or Ir and based on the total weight of the organopolysiloxanes (A), (B) or (C).

The preferred transition metal-containing organosiloxanes (D) are those organosiloxanes which comprise at least one chemically bonded transition metal complex of Pt, Pd, Rh, Ru, Os or Ir and which are built up of at least three units of the formula $$G_mR_nSiO_{\frac{4-n-m}{2}} , \quad (6)$$

in which
G is a radical of the formula $$MY_hZ_i \quad (7),$$

where
M is Pt, with the exception of Pt(O), Pd, Rh, Ru, Os or IR,
Y are identical or different ligands selected from the group consisting essentially of Cl, Br, I, $NH_3$, $PR_3$, H, CO, 1,5-cyclooctadiene, pyridine, bipyridine, acetate, acetylacetonate, phenyl cyanide, ethylenediamine, acetonitrile, 2,5-norbornadiene, nitrate, nitrite, $H_2O$, benzene, diphenylphosphinoethane, 1,3-divinyl-1,1,3,3-tetramethyldisiloxane and alkenes having from 1 to 18 carbon atoms, are identical or different ligand radicals selected from the group consisting of $Sp-NR^3_2$, $Sp-NR^3(R^4)NR^3_2$, Sp-4-pyridine, Sp-4-bipyridine, $Sp-PR^3(R^4)PR^3_2$, $Sp-PR^3_2$, $Sp-POR^3_2$, $Sp-P(OR^3)_2$ and $Sp-SR^3$,
$R^3$ is a hydrogen atom or a radical R,
$R^4$ is a divalent hydrocarbon radical having from 1 to 8 carbon atoms per radical,
Sp is a divalent, SiC-bonded, substituted or unsubstituted hydrocarbon radical having from 1 to 18 carbon atoms per radical,
R is a monovalent, substituted or unsubstituted hydrocarbon radical having from 1 to 18 carbon atoms per radical,
h is an integer from 1 to 8,
i is 1, 2, 3 or 4 and
m and n are identical or different and are each 0 or an integer from 1 to 3 and n+m≧1, with the proviso that at least one radical G is present in the organosiloxane.

Examples of hydrocarbon radicals R and $R^3$ are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radical such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; and octadecyl radicals such as the n-octadecyl radical; cycloalkyl radicals such as the cyclohexyl radical; alkenyl radicals such as the vinyl, 1-propenyl, 1-butenyl, 2-butenyl, allyl, iso-butenyl, 1-pentenyl and 2-methyl-1-butenyl radical; alkynyl radicals such as the ethynyl, propargyl, 1-propynyl and 1-butynyl radical, and aralkyl radicals such as the benzyl radical and the α- and β-phenylethyl radical; with alkyl radicals being preferred.

Examples of substituted hydrocarbon radicals are haloalkyl radicals such as the 3,3,3-trifluoro-n-propyl radical, the 2,2,2,2',2',2'-hexafluoroisopropyl radical, the heptafluoroisopropyl radical, the 3-chloro-n-propyl radical, 2-ethyl bromide and 3-propyl bromide and haloaryl radicals such as the o-, m- and p-chlorophenyl radical, o-, m- and p-bromophenyl radical.

Examples of divalent hydrocarbon radicals Sp are saturated alkylene radicals such as the methylene and ethylene radical and also propylene, butylene, pentylene, hexylene, cyclohexylene and octadecylene radicals or unsaturated alkylene or arylene radicals such as the hexenylene radical and phenylene radicals.

Examples of divalent hydrocarbon radicals $R^4$ are the examples having from 1 to 8 carbon atoms given for Sp.

Examples of preferred alkenes as ligands Y are 1-octene, 1-hexene and 2-butene.

Preferred ligand radicals Z are $Sp\text{-}NR^3{}_2$ and $Sp\text{-}NR^3(R^4)NR^3{}_2$, with $R^3$ being a hydrogen atom or an alkyl radical having from 1 to 6 carbon atoms and $R^4$ being an alkylene radical.

i is preferably 1 and n is preferably 1 and 2.

In particular, the organosiloxanes (D) are linear and preferably terminated by $G_m$.

The preferred transition metals M are Pt, Pd and Rh.

The invention also provides a transition metal-containing organopolysiloxane composition comprising (A) compounds which comprise radicals having aliphatic carbon-carbon multiple bonds, (B) compounds having Si-bonded hydrogen atoms selected from among silanes or siloxanes, or, instead of (A) and (B), (C) compounds having aliphatic carbon-carbon multiple bonds and Si-bonded hydrogen atoms, and (D) as hydrosilylation catalyst, transition metal-containing organosiloxanes which comprise at least one transition metal complex, chemically bonded via ligands selected from among amino, phosphino or sulfido groups, of Pt, Pd, Rh, Ru, Os or Ir with the exception of Pt(O).

The components (A), (B), (C) and (D) present in the above hydrosilylation process are also preferred in the organopolysiloxane composition.

Although not preferred, inhibitors can also be used in the hydrosilylation process and in the organopolysiloxane composition. Examples of the inhibitors are 1,3-divinyl-1,1,3,3-tetramethyldisiloxane, benzotriazole, dialkylformamides, alkylthioureas, methyl ethyl ketoxime, organic or organosilicon compounds having a boiling point of at least 25° C. at 1012 mbar (abs.) and at least one aliphatic triple bond in accordance with U.S. Pat. No. 3,445,420 such as 1-ethynyl-cyclohexan-1-ol, 2-methyl-3-butyne-2-ol, 3-methyl-1-pentyne-3-ol, 2,5-dimethyl-3-hexyne-2,5-diol and 3,5-dimethyl-1-hexyne-3-ol, inhibitors in accordance with U.S. Pat. No. 2,476,166, such as a mixture of diallyl maleate and vinyl acetate, and inhibitors in accordance with U.S. Pat. No. 4,504,645, such as maleic monoesters.

The invention also provides a process for preparing transition metal-containing organosiloxanes (D1) which comprise at least one transition metal complex, chemically bonded via ligands selected from among amino, phosphino or sulfido groups, of Pt, Pd, Rh, Ru, Os or Ir, where a transition metal compound of the central atoms Pt, Pd, Rh, Ru, Os and Ir which possesses at least one weak ligand situated below amino, phosphino and sulfido ligands in the spectrochemical series, is reacted with an organosiloxane of at least three organosiloxane units which possesses at least one bonded amino, phosphino or sulfido group.

The ligand which is weak according to the spectrochemical series and is bonded to the central transition metal atom improves the solubility of the transition metal compound and can easily be replaced by the strong, organosiloxane-bonded ligands. The organosiloxanes (D1) can be prepared in a simple way in good yields, for example by simple mixing of the transition metal compound with the organosiloxane possessing at least one bonded amino, phosphino or sulfido group.

Those ligands on the transition metal compound of the central atoms Pt, Pd, Rh, Ru, Os and Ir possessing at least one weak ligand which are not replaced in the process can be either weak or strong ligands.

In a preferred process for preparing organosiloxane (D1) which are built up of at least three units of the general formula

  (8)

in which

A is a radical of the general formula

  (9), in which transition metal compounds of the formula

  (10), are reacted with organosiloxanes of at least three units of the formula

  (11)

where $M^1$ is Pt, Pd, Rh, Ru, Os or Ir,

X are identical or different and are ligands selected from the group consisting of Cl, Br, I, H, CO, 1,5-cyclooctadiene, acetate, acetylacetonate, phenyl cyanide, acetonitrile, 2,5-norbornadiene, nitrate, nitrite, $H_2O$, benzene, diphenylacetylene, ethylene, 1-octene, 1-hexene and 1,3-divinyl-1,1,3,3-tetramethyldisiloxane, k is 1, 2, 3 or 4 and Y, Z, R, h, i, m and n are as defined above.

Preferred weak ligands X are cyclooctadiene, norbornadiene, 1-octene, ethylene and diphenylacetylene.

Examples of transition metal compounds which can be used in the process of the invention are $PtCl_2$, $PtI_3$, $[(C_6H_5)_3P]_2PtCl_2$, $[(C_2H_5)_3P]_2PtCl_2$, $PtCl_4$, $Pt(H_2NCH_2CH_2NH_2)Cl_2$, $Pt(NH_3)_2Cl_2$, $PtBr_2$, 1,5-cyclooctadiene. $PtCl_2$, $Pd(CH_3CN)_2Cl_2$, $PdBr_2$, 1,5-cyclooctadiene.$PdCl_2$, $[(C_6H_5)_3P]_2PdCl_2$, $PdCl_2$, $RuCl_3$, $Ru(NH_3)_6Cl_2$, $[(C_6H_5)_3P]_3RuCl_2$, $RhCl_3$, $RhBr_3$, $[(C_6H_5)_3P]_3RhCl$, (1,5-cyclooctadiene)$_2$Pt, bis(diphenylacetylene)platinum, reaction products of transition metal halides with olefins, ethylenedichloroplatinum, 1,3-divinyl-1,1,3,3-tetramethyldisiloxaneplatinum complexes (e.g. $Pt_2[1,3$-divinyl-1,1,3,3-tetramethyldisiloxane]$_3$), Pd[bis-(1,2-diphenylphosphinoethane)], hexarhodium hexadecacarbonyl and triruthenium dodecacarbonyl, with preference being given to 1,5-cyclooctadiene.$PtCl_2$, 1,5-cyclooctadiene-$PdCl_2$, $Ru(NH_3)_6Cl_2$, (1,5-cyclooctadiene)$_2$Pt, ethylenedichloroplatinum, 1,3-divinyl-1,1,3,3-tetramethyldisiloxaneplatinum complex, bis(diphenylacetylene)platinum, and also reaction products of transition metal halides with olefins.

Particularly preferred transition metal compounds are 1,5-cyclooctadiene.$PtCl_2$, bis(diphenylacetylene)platinum and the reaction products of 1-octene with platinum chlorides. The preferred transition metal is platinum in the oxidation state II.

The process for preparing the organosiloxanes (D1) is preferably carried out in the presence of organic solvents such as n-hexane, toluene, methylene chloride, chloroform, acetone, methanol, ethanol, isopropanol or preferably tetrahydrofuran (THF).

The process for preparing the organosiloxanes (D1) is preferably carried out at temperatures of from 20° C. to 120° C., and preferably at the pressure of the surrounding atmosphere. The organic solvent or the mixture of organic solvent and replaced ligand is preferably removed after the reaction.

Further ligands present on the transition metal of the organosiloxanes (D1) can be replaced by other ligands in a subsequent polymer-analogous reaction. Thus, chloro ligands present can be replaced by acetylacetonate, glycolate or oxalate ligands.

In the following examples, unless otherwise indicated,
(a) all amounts are by weight;
(b) all pressures are 0.10 mPa (abs.);
(c) all temperatures are 20° C. and
(d) "of Th." is the abbreviation for "of theory".

Preparation of the polymer catalysts

EXAMPLE 1

50.90 g of cyclooctadieneplatinum dichloride (136 mmol of platinum) were dissolved in 2.8 liters of THF and initially charged at 64° C. 362.7 g of a polydimethylsiloxane terminated by $\alpha,w$-aminoethylaminopropyl groups (0.75 mmol of amine function per gram) and having a viscosity of 200 mPa.s were then metered in over a period of 1 hour and the mixture was stirred for an additional 2 hours under reflux. After cooling to room temperature, the yellow liquid was filtered.

2764.9 g of a clear product (polymer catalyst 1) containing 0.72% by weight of platinum were obtained (yield: 75% of Th. based on platinum).

EXAMPLE 2

31.46 g of a solution of 1-octeneplatinum dichloride in 1-octene containing 3.8% by weight of platinum (6.127 mmol of platinum) were mixed with 200 ml of toluene and subsequently mixed with 46.94 g of a polydimethylsiloxane terminated by $\alpha,w$-aminoethylaminopropyl groups (0.258 mmol of amine function per gram) and having a viscosity of 691 mPa.s.

The solution was stirred for 8 hours at 70° C., cooled to room temperature and filtered. The filtrate was evaporated to constant weight at 60° C. in a high vacuum. 75.2 g of a dark yellow, highly viscous product (polymer catalyst 2) containing 1.54% by weight of platinum were obtained (yield: 97% of Th. based on platinum).

EXAMPLE 3

3.379 g of bis(diphenylacetylene)platinum (6.127 mmol of platinum) were dissolved in 200 ml of toluene and mixed with 46.94 g of polydimethylsiloxane terminated by $\alpha,w$-aminoethylaminopropyl groups (0.258 mmol of amine function per gram) and having a viscosity of 691 mPa.s. The solution was stirred for 8 hours at 70° C., cooled to room temperature and filtered. The filtrate was evaporated to constant weight at 60° C. in a high vacuum. 48.6 g of a yellow, highly viscous product (polymer catalyst 3) containing 1.35% by weight of platinum were obtained (yield: 85% of Th. based on platinum).

EXAMPLE 4

3.58 g of cylooctadieneplatinum dichloride (9.56 mmol of platinum) were dissolved in 50 ml of THF and mixed with 5.22 g of a polydimethylsiloxane terminated by $\alpha,w$-aminopropyl groups (1.83 mmol of amine function per gram) and having a viscosity of 14 mPa.s. The solution was stirred for 6 hours at 64° C., cooled to room temperature and filtered. The filtrate was evaporated to constant weight at 60° C. in a high vacuum. 6.82 g of a yellow, brittle product (polymer catalyst 4) containing 26.2% by weight of platinum were obtained (yield: 96% of Th. based on platinum).

EXAMPLE 5

0.757 g of dichlorocyclooctadienepalladium (2.65 mmol of palladium) were dissolved in 50 ml of THF and mixed with 7.06 g of a polydimethylsiloxane terminated by $\alpha,w$-aminoethylaminopropyl groups (0.75 mmol of amine function per gram) and having a viscosity of 200 mPa.s. The solution was stirred for 6 hours at 64° C. under reflux, cooled to room temperature and filtered.

The filtrate was evaporated to constant weight at 60° C. in a high vacuum. 7.2 g of a highly viscous, light brown product (polymer catalyst 5) containing 3.5% by weight of palladium were obtained (yield: 88% of Th. based on palladium).

EXAMPLE 6

5.09 g of cyclooctadieneplatinum dichloride (13.6 mmol of platinum) were dissolved in 50 ml of THF and mixed with 36.27 g of a polydimethylsiloxane terminated by $\alpha,w$-aminoethylaminopropyl groups (0.75 mmol of amine function per gram) and having a viscosity of 200 mPa.s. The solution was stirred for an additional 6 hours at 64° C., 3.76 g (27.2 mmol) of potassium acetylacetonate were added and the mixture was heated to boiling for 6 hours at 64° C. After filtration at room temperature, the filtrate was evaporated to constant weight at 60° C. in a high vacuum. 34.3 g of a yellow, brittle product (polymer catalyst 6) containing 6.8% by weight of platinum were obtained (yield: 88% of Th. based on platinum).

Hydrosilylation

EXAMPLE 7

45.75 mg of polymer catalyst 2, the preparation of which has been described in Example 2, were dissolved in 1 ml of toluene and then added to 6.83 g of $\alpha,w$-divinyldimethylpolysiloxane having a viscosity of 500 mPa.s at 25° C. The solvent was removed at room temperature under reduced pressure. To the remaining reaction mixture was added 0.17 g of a mixed polymer of trimethylsiloxane and hydrogenmethylsiloxane units having a viscosity of 33 mPa.s at 25° C. and containing 1.12% by weight of Si-bonded hydrogen, so that the mixture contained 100 ppm by weight of platinum, calculated as element. At room temperature, the total mixture was stable for 2.75 hours. After heating for 6.3 minutes at 60° C., complete cross-linking could be achieved. A transparent product insoluble in organic solvents was obtained.

EXAMPLE 8

140 g (0.85 mol) of hydrogentriethoxysilane were mixed with 100 g (0.88 mol) of allyl glycidyl ether and 10 g of this mixture, together with 141.2 mg of polymer catalyst 6, were initially charged in a reaction vessel at 95° C. under atmospheric pressure.

On adding the remainder of the above mentioned mixture dropwise over a period of 70 minutes, the temperature rose to 150° C. After complete addition, the reaction mixture is stirred for an additional 30 minutes at 150° C. After distillation, 3-glycidoxypropyltriethoxysilane was obtained as a colorless, liquid product in 75.3% yield.

EXAMPLE 9

180 g of a mixed polymer of trimethylsiloxane and hydrogenmethylsiloxane units having a viscosity of 24.4 mPa.s at 25° C. and containing 1.60% by weight of Si-bonded hydrogen were heated with 32.0 g (0.271 mol) of α-methylstyrene and 0.51 g of polymer catalyst 1, the preparation of which has been described in Example 1, to 120° C. while stirring and with nitrogen blanketing. Subsequently, 31.4 g (0.266 mol) of α-methylstyrene were metered in over a period of 10 minutes and the mixture was allowed to react for 1.5 hours. 493 g (2.929 mol) of 1-dodecene were then added dropwise over a period of 30 minutes and the mixture was further stirred for 1 hour at 120° C. To remove volatile constituents, the reaction mixture was heated at 160° C. in a high vacuum for 4 hours. After filtration, 633 g (85.9% of Th.) of a clear oil having a viscosity of 1200 mPa.s and an Apha color number of 50 in accordance with DIN ISO 6271 were obtained.

EXAMPLE 10

17.9 g (0.07 mol) of trimethylsilyl 10-undecenoate were heated together with 40 g of a mixed polymer of trimethylsiloxane, dimethylsiloxane and methylsiloxane units having a viscosity of 238 mPa.s at 25° C. and containing 0.025% by weight of Si-bonded hydrogen, and 242.1 mg of polymer catalyst 3, the preparation of which is described in Example 3, to 100° C. while stirring and under protective gas. Subsequently, a further 160 g of the above mentioned mixed polymer were metered in over the course of 1 hour. After a reaction time of 1 hour at a temperature of 100° C., another 80.7 mg of polymer catalyst 3 were added and the mixture reacted for an additional hour at 100° C. 260 g (99% of Th.) of a clear oil having a viscosity of 520 mPa.s at room temperature and an Apha color number of 150 in accordance with DIN ISO 6271 were obtained.

COMPARATIVE EXAMPLE 11

A Polysiloxane-bonded platinum catalyst analogous to that described in U.S. Pat. No. 3,795,656, which is used as intermediate in analogy with U.S. Pat. No. 4,398,010.

10 g of an α,w-(aminomethylaminopropyl)polydimethylsiloxane having an average chain length of 70, an amine number of 0.75 and a viscosity of 119 mm²/s were stirred with 1.8 g of hexachloroplatinic acid ($H_2PtCl_6 \times H_2O$; Pt: 40% by weight) in a mixture of 125 g of toluene and 20 g of ethanol for 2 hours at 25° C. Despite the large amount of solvent, no completely homogeneous solution was obtained. The orange mixture contained gel-like particles. The above mentioned amount and composition of the solvent mixture did give the best solution behavior.

After evaporation of the solvent mixture at 30° C./1 mbar, 11.8 g of an orange solid were obtained. The evaporation was extremely difficult since strong foaming occurred.

Polysiloxane-bonded platinum catalyst analogous to that described in U.S. Pat. No. 4,398,010 by reaction of the product from A with divinyltetramethyldisiloxane and $NaHCO_3$ in ethanol.

The ratios used of the starting materials are selected in analogy with U.S. Pat. No. 4,298 010.

11.8 g of the product from A were slurried in 11.8 g of ethanol and, since no homogeneous solution was formed, mixed with 0.35 g of sodium hydrogen carbonate and 1.2 g of divinyltetramethyldisiloxane and stirred for 2 hours under reflux. Subsequently, the mixture was stirred for about 15 hours at room temperature. An orange, nonhomogeneous mixture was obtained. After addition of about 20 g of tetrahydrofuran, the mixture was mostly homogeneous. Subsequently, the insoluble solids and salts were filtered off and the filtrate was evaporated at 30° C./1 mbar. 12 g of an orange solid were obtained.

What is claimed is:

1. A transition metal-containing organosiloxane having at least three organosiloxane units, which comprises at least one transition metal complex, chemically bonded via ligands selected from the group consisting of amino, phosphino or sulfido groups, of Pt, Pd, Rh, Ru, Os or Ir, excluding those organosiloxanes which contain exclusively Pt(O) complexes bonded via amino ligands.

2. A transition metal-containing organosiloxane as claimed in claim 1, which comprises at least one chemically bonded transition metal complex of Pt, Pd, Rh, Ru, Os or Ir and which is built up of at least three units of the formula $$G_m R_n SiO_{\frac{4-n-m}{2}}, \quad (6)$$

in which
G is a radical of the formula $$MY_h Z_i \quad (7)$$

where
M is Pt, with the exception of Pt(O), Pd, Rh, Ru, Os or Ir,
Y are identical or different and are ligands selected from the group consisting of Cl, Br, I, $NH_3$, $PR_3$, H, CO, 1,5-cyclooctadiene, pyridine, bipyridine, acetate, acetylacetonate, phenyl cyanide, ethylenediamine, acetonitrile, 2,5-norbornadiene, nitrate, nitrite, $H_2O$, benzene, diphenylphosphinoethane, 1,3-divinyl-1,1,3,3-tetramethyldisiloxane and alkenes having from 1 to 18 carbon atoms,
Z are identical or different and are ligand radicals selected from the group consisting of $Sp-NR^3_2$, $Sp-NR^3(R^4)NR^3_2$, $Sp$-4-pyridine, $Sp$-4-bipyridine, $Sp-PR^3(R^4)PR^3_2$, $Sp-PR^3_2$, $Sp-POR^3_2$, $Sp-P(OR^3)_2$ and $Sp-SR^3$,
$R^3$ is a hydrogen atom or a radical R,
$R^4$ is a divalent hydrocarbon radical having from 1 to 8 carbon atoms per radical,
Sp is a divalent, SiC-bonded, substituted or unsubstituted hydrocarbon radical having from 1 to 18 carbon atoms per radical,
R is a monovalent, substituted or unsubstituted hydrocarbon radical having from 1 to 18 carbon atoms per radical,
h is an integer from 1 to 8,
i is 1, 2, 3 or 4 and
m and n are identical or different and are each 0 or an integer from 1 to 3 and $n+m \geq 1$, with the proviso that at least one radical G is present in the organosiloxane.

3. A hydrosilylation process which comprises reacting
(A) compounds containing radicals having aliphatic carbon-carbon multiple bonds, and (B) compounds having Si-bonded hydrogen atoms selected from silanes or siloxanes, in the presence of (D) transition metal-containing organosiloxanes as claimed in claim 1.

4. An organopolysiloxane composition comprising (A) compounds containing radicals having aliphatic carbon-carbon multiple bonds, (B) compounds having Si-bonded hydrogen atoms seized from silanes or siloxanes, and (D) transition metal-containing organosiloxanes as claimed in claim 1.

5. A process for preparing transition metal-containing organosiloxanes of at least three organosiloxane units, which comprise at least one transition metal complex, chemically bonded via ligands selected from the group consisting of amino, phosphino or sulfido groups of Pt, Pd, Rh, Ru, Os or Ir, which comprises reacting a transition metal compound of the central atoms Pt, Pd, Rh, Ru, Os and Ir which possesses at least one weak ligand situated below amino, phosphino and sulfido ligands in the spectrochemical series, with an organosiloxane of at least three organosiloxane units which possesses at least one bonded amino, phosphino or sulfido group.

6. The process as claimed in claim 5 for preparing transition metal-containing organosiloxanes which are built up of at least three units of the formula $$A_m R_n SiO_{\frac{4-n-m}{2}}, \quad (8)$$

in which
A is a radical of the general formula $$M^1 Y_h Z_i \quad (9),$$

in which transition metal compounds of the formula $$M^1 Y_h X_k \quad (10),$$

are reacted with organosiloxanes of at least three units of the formula $$Z_m R_n SiO_{\frac{4-n-m}{2}}, \quad (11)$$

where
$M^1$ is Pt, Pd, Rh, Ru, Os or Ir,

X are identical or different and are ligands selected from the group consisting of Cl, Br, I, H, CO, 1,5-cyclooctadiene, acetate, acetylacetonate, phenyl cyanide, acetonitrile, 2,5-norbornadiene, nitrate, nitrite, $H_2O$, benzene, diphenyl acetylene, ethylene, 1-octene, 1-hexene and 1,3-divinyl-1,1,3,3-tetramethyldisiloxane, k is 1, 2, 3 or 4, Y are idential or different and are ligands selected from the group consisting of Cl, Br, I, $NH_3$, $PR_3$, H, CO, 1,5-cyclooctadiene, pyridine, bipyridine, acetate, acetylacetonate, phenyl cyanide, ethylenediamine, acetonitrile, 2,5-norbornadiene, nitrate, nitrite, $H_2O$, benzene, diphenylphosphino ethane, 1,3-divinyl-1,1,3,3-tetramethyldisiloxane and alkenes having from 1 to 18 carbon atoms, Z are identical or different and are ligand radicals selected from the group consisting of $Sp-NR^3_2$, $Sp-NR^3(R^4)NR^3_2$, $Sp-4$-pyridine, $Sp-4$-bipyridine, $Sp-PR^3(R^4)PR^3_2$, $SP-PR^3_2$, $Sp-POR^3_2$, $Sp-P(OR^3)_2$ and $Sp-Sr^3$, $R^3$ is a hydrogen atom or a radical R, $R^4$ is a divalent hydrocarbon radical having from 1 to 8 carbon atoms per radical, Sp is a divalent, SiC-bonded, substituted or unsubstituted hydrocarbon radical having from 1 to 18 carbon atoms per radical, R is a monovalent, substituted or unsubstituted hydrocarbon radical having from 1 to 18 carbon atoms per radical, h is an integer from 1 to 8, i is 1, 2, 3 or 4 and m and n are identical or different and are each 0 or an integer from 1 to 3 and $n+m \geq 1$, with the proviso that at least one radical A is present in the organosiloxane.

7. A hydrosilation process which comprises reacting compounds having aliphatic carbon-carbon multiple bonds and Si-bonded hydrogen atoms, in the presence of transition metal-containing organosiloxanes as claimed in claim 1.

8. An organopolysiloxane composition comprising

C. compounds having aliphatic carbon-carbon multiple bonds and Si-bonded hydrogen atoms, and D. transition metal-containing organosiloxanes as claimed in claim 1.

* * * * *